United States Patent [19]

Grevious

[11] Patent Number: 5,168,871
[45] Date of Patent: Dec. 8, 1992

[54] METHOD AND APPARATUS FOR PROCESSING QUASI-TRANSIENT TELEMETRY SIGNALS IN NOISY ENVIRONMENTS

[75] Inventor: John Grevious, Minneapolis, Minn.

[73] Assignee: Medtronic, Inc., Minneapolis, Minn.

[21] Appl. No.: 612,046

[22] Filed: Nov. 9, 1990

[51] Int. Cl.$^5$ ............................................. A61N 1/362
[52] U.S. Cl. .............................. 128/419.0 PT; 128/903
[58] Field of Search ............ 128/419.0 PG, 419.0 PT, 128/696, 903

[56] References Cited

U.S. PATENT DOCUMENTS

| | | | |
|---|---|---|---|
| 4,494,545 | 1/1985 | Slocum et al. | 128/903 |
| 4,550,731 | 11/1985 | Batina et al. | 128/903 |

Primary Examiner—William E. Kamm
Attorney, Agent, or Firm—John A. Rissman; Harold R. Patton

[57] ABSTRACT

A software-controlled, external programmer for transcutaneously programming and receiving data from an implanted medical device providing enhanced discrimination and detection of pulse-interval-coded signals of interest telemetered out of the implanted medical device from undesirable transient and steady-state noise. The programmer incorporates a detector including an active mixer and a precision tuned active phase shifting network providing low level signal rectification, precise narrow bandpass filtering, and 30 decibels of amplification. At the detector, the received signal is mixed with a phase shifted version of itself to produce a detected DC component which is a function of frequency. The DC response emulates a system with a narrow 25 kHz bandpass filter operating at 175 kHz, but does not share its undesirable transient response. For signals in the reject band, the output produces a signal of the opposite polarity of the signals within the pass bands. Transient0 noise excites the receiver antenna and produces a ringing response accompanied by components above 400 kHz. The noise response of the antenna stimulates the detector to produce the intended inverted output. As the transient noise amplitude increases, the inverted response increases in amplitude driving the output level further away from the trigger level of a post-detection comparator. Similarly, any steady state noise signal in the reject band will also result in a steady state inverted response that does not trigger the comparator.

8 Claims, 8 Drawing Sheets

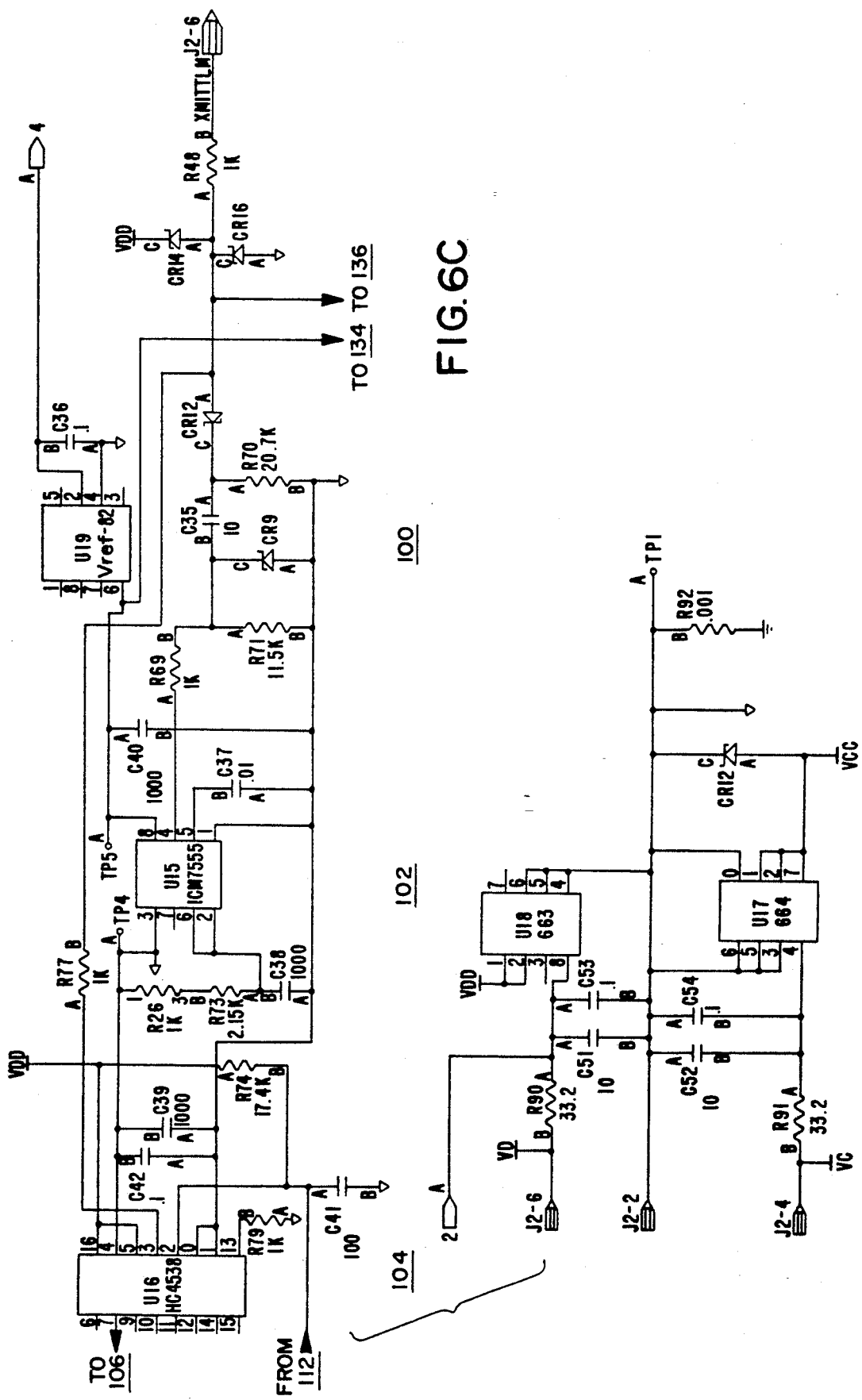

METHOD AND APPARATUS FOR PROCESSING QUASI-TRANSIENT TELEMETRY SIGNALS IN NOISY ENVIRONMENTS

CROSS REFERENCE TO RELATED APPLICATION

Attention is drawn to the following related, commonly assigned U.S. Patent application Ser. No. 07/611,900 filed on Nov. 9, 1980, in my name, entitled CLOSED LOOP TRANSMITTER FOR MEDICAL IMPLANT incorporated herein by reference.

BACKGROUND OF THE INVENTION

1. Field of the Invention

This invention relates to a method and apparatus for detecting and discriminating a pulse code modulated RF signal transmitted from an implanted medical device to a medical device programmer from transient and steady state noise. 2. Description of the Prior Art In the field of programmable implanted medical devices, such as cardiac pacemakers, tachyarrhythmia-control devices, implantable drug dispensers and nerve stimulators, it has become common to provide an interactive, transceiver system for both remotely programming operating functions, modes and parameters of the implanted device, and telemetering out data related thereto on command by RF telemetry. In nearly all such active, electronic, implanted medical devices, it has become highly desirable to have the ability to reprogram the device's modes of operation, parameters and other functions and to monitor the performance of the device, both historically and contemporaneously. Such current medical devices are designed to provide two-way telemetry by radio frequency signal transmission between the implanted device and the programming head or wand of the external programmer to provide for the exchange of binary-coded transmitted information to enable the aforementioned programming by telemetry in and the reading out of data stored in the device by telemetry out.

For example, the Medtronic U.S. Pat. No. 4,253,466 describes an implantable digital, programmable, cardiac pacemaker pulse generator which may be programmed by the programmer described in Medtronic U.S. Pat. No. 4,250,884, both incorporated herein by reference. Such programmers as disclosed in the '884 patent are microprocessor-based and menu-driven under an overall operating routine and subroutines. Such programmers display operating conditions, commands and error messages to prompt the user in the proper use of the programming system. The system of the '466 and '884 patent sets forth the software-controlled programming of a series of Medtronic ® implantable pacemakers (IPG's), but it does not describe the uplink telemetry out on command of the external programmer of the programmed commands, electrogram, end of-life indicators and the like that have been developed and implemented in subsequent pacing systems.

More recently, microprocessor-based programmers have been developed by Medtronic, Inc. and others which are operated under the control of dedicated, plug-in ROM modules to enable the operation of the system with regard to specific model or series of models of implanted pulse generators. In such systems, the programmer is incapable of operating until a plug-in module or cartridge has been properly installed. The Medtronic ® MemoryMod ™ cartridge enables the physician to apply the programmer to a specific set of pulse generator models. The software cartridge concept allows Medtronic, Inc. to expand and update the application of the programmer to new pulse generators and functional capabilities as they become available.

In current implanted pacemakers, confirmation of a programming transmission occurs by automatic uplink transfer of data via telemetry out. Use of an ECG cable and electrode leads is not required for programming confirmation with these devices. However, if telemetry is not received because of strong electrical interference, the programmer will attempt to confirm the transmission by surface detection of the PCI (program confirmation indicator) issued by the IPG. This method of program confirmation can occur only if the programmer is connected to electrodes on the patient. As described below the present invention discloses improvements which are directed toward the reduction or elimination of failures in telemetry out because of strong electrical interference.

Furthermore, advanced programming and telemetry systems envisage the transmission of the patient's electrogram directly from the pacing electrodes in contact with the heart to the programmer via the RF telemetry link in order to provide near-field and/or far-field electrograms directly from the myocardium. In such systems, the effects of electrical interference and other noise on the telemetry transmission is of concern. Medtronic U.S. Pat. No. 4,556,063 (incorporated herein by reference) describes such a system for telemetering out both digital and analog data.

The presence of electrical interference or noise strong enough to interrupt reception of telemetry from the implanted pulse generator can affect operation of and telemetry functions, including programming confirmation.

Hospital operating rooms, catherization laboratories and even physicians' offices are often noisy electrical environments, and such noise has been found on occasion to interfere with the proper programming or interrogation of an implanted pacemaker. Such programming and interrogation of the implanted pacemaker's function is commonly undertaken as part of the surgical implant of the implanted pulse generator. Other equipment in the operating room or in adjoining rooms or floors of the facility may generate severe electrical noise. To ensure the safety of the patient, prior systems, as explained above have been designed conservatively to avoid misprogramming once acquisition has been obtained by closure of a reed switch within the implanted pulse generator.

In the prior art systems referenced above, the physician was instructed to either identify the source of interference and eliminate it or move the patient and programmer to another location to avoid its effects. In addition, software controllable gain control circuitry was provided which attempted to optimize the gain in the presence of interference to pick up only telemetered-out RF signals and exclude the noise or interference.

In response to the above-described disadvantages of the prior art systems, attempts have been made to provide automatic gain control circuitry (see for example, U.S. Pat. No. 4,562,840 and software subroutines e.g., those within the Medtronic ® MemoryMod cartridges, and specifically disclosed in Medtronic U.S. Pat. No. 4,531,523, incorporated herein by reference.

The Maltronic® 9710 programmer and improved models of that programmer provided circuitry of the type depicted in Medtronic U.S. Pat. No. 4,542,532, for detecting a telemetry signal by use of a receiver input circuit tuned to the 175 kHz center frequency and a bandpass filter and manual gain control. The signal developed in the receiver circuit is further processed in conjunction with the software implemented gain control referenced above. The transceiver of the '532 Patent implemented, a dual antennae, to reject essentially far-field noise which tends to link both coils with the same field strength. As explained in the '532 Patent, since, in the receive mode, the two coils are wound in series opposition, the noise field component from the remote noise source would be cancelled, leaving primarily the signal component at the input of the receiver.

However, deficiencies in the filtering circuit of the '532 Patent as implemented in the Model 9710 series programming system have continued to cause difficulty in the reception of radio frequency pulse code modulated signals transmitted from the implanted pacemakers.

The problems with artifact noise have been addressed with software algorithms as referenced above. However, it is desirable to so design the circuitry as to substantially reduce the remaining problems with transient and steady state noise.

SUMMARY OF THE INVENTION

Difficulties and deficiencies associated with the prior detection and discrimination circuitry with respect to telemetered signal detection in the presence of noise are alleviated and corrected in accordance with the present invention by a telemetry receiver circuit which employs phase shifting and mixing stages coupled to a tuned antenna circuit deliberately tuned outside the pulse frequency pass band for amplifying received telemetry signals and attenuating noise signals coupling the tuned antenna circuit.

Thus, in telemetry receiver circuit receiving radio frequency signals which are representative of either analog or digital values and wherein said radio frequency signal is either emitted from or induced in an inductive-capacitive tuned antenna circuit, the improvement of the present invention for detecting and discriminating received data signals from noise signals that generate a ringing response of said inductive-capacitive tuned antenna circuit comprises: means for amplifying RF signals emitted from or generated within said inductive-capacitive tuned antenna circuit and providing an amplified RF signal; means responsive to said amplified RF signal for shifting its phase and for providing a phase shifted, amplified RF signal; means for mixing said phase shifted, amplified RF signal with said amplified RF signal for providing a detected DC component of said RF amplified signal, the amplitude of which is a function of frequency; means for establishing a threshold amplitude value; and means for comparing the amplitude of said DC component with said threshold amplitude for providing a detected and demodulated output signal discriminated from noise signals.

The present invention include a detector incorporating an active mixer and a precision tuned active phase shifting network. The detector provides low level signal rectification, precise narrow bandpass filtering, and 30 decibels of amplification At the detector, the received signal is mixed with a phase shifted version of itself to produce a detected DC component which is a function of frequency. The DC response emulates a system with a narrow 25 kHz bandpass filter operating at 175 kHz, but does not share its undesirable transient response. For signals in the reject band, the output produces a signal of the opposite polarity of the signals within the pass band. The receiver antenna is tuned below 148 kHz with a Q still high enough to allow reasonable amplitude response at 175 kHz. Transient noise exciting the antenna produces a ringing response at the tuned frequency in the receiver coils. The noise response of the antenna stimulates the detector to produce the intended inverted output. As the transient noise amplitude increases, the inverted response increases in amplitude driving the output level further away from the trigger level of a post-detection comparator. Similarly, any steady state noise signal in the response that does not trigger the comparator.

BRIEF DESCRIPTION OF THE DRAWINGS

These and other features and advantages of the present invention will become more apparent by referring to the following detailed description and accompanying drawings in which:

FIGS. 6A–6C constitute a detailed circuit schematic of the RF telemetry receiving and transmitting circuitry of FIG. 4.

DESCRIPTION OF THE PREFERRED EMBODIMENT OF THE INVENTION

It will be understood that the detector and discrimination circuitry of the present invention as depicted hereafter in conjunction with FIGS. 4 through 6A–6C, may be employed with a programmer of a configuration that differs from the Medtronic® Model 9710 programmer configuration described hereinbefore. For example, the improved programming head circuitry of the present invention may be employed in conjunction with a more powerful, computer based programming system of the type designated as the Medtronic® Model 9760 programmer wherein software dedicated to specific implanted pacemaker pulse generator models may be implemented in floppy diskettes rather than ROM cartridges. In addition, the programming system may employ a video monitor and enhanced keyboard or light pen or mouse in substitution for the LCD and keyboard of the programmer 10 depicted in FIG. 1. These and other modifications of the overall programming system may be employed with the enhanced transceiver circuitry of the present invention, which is designated the Medtronic® Model 9765 programming head.

Figure 4:
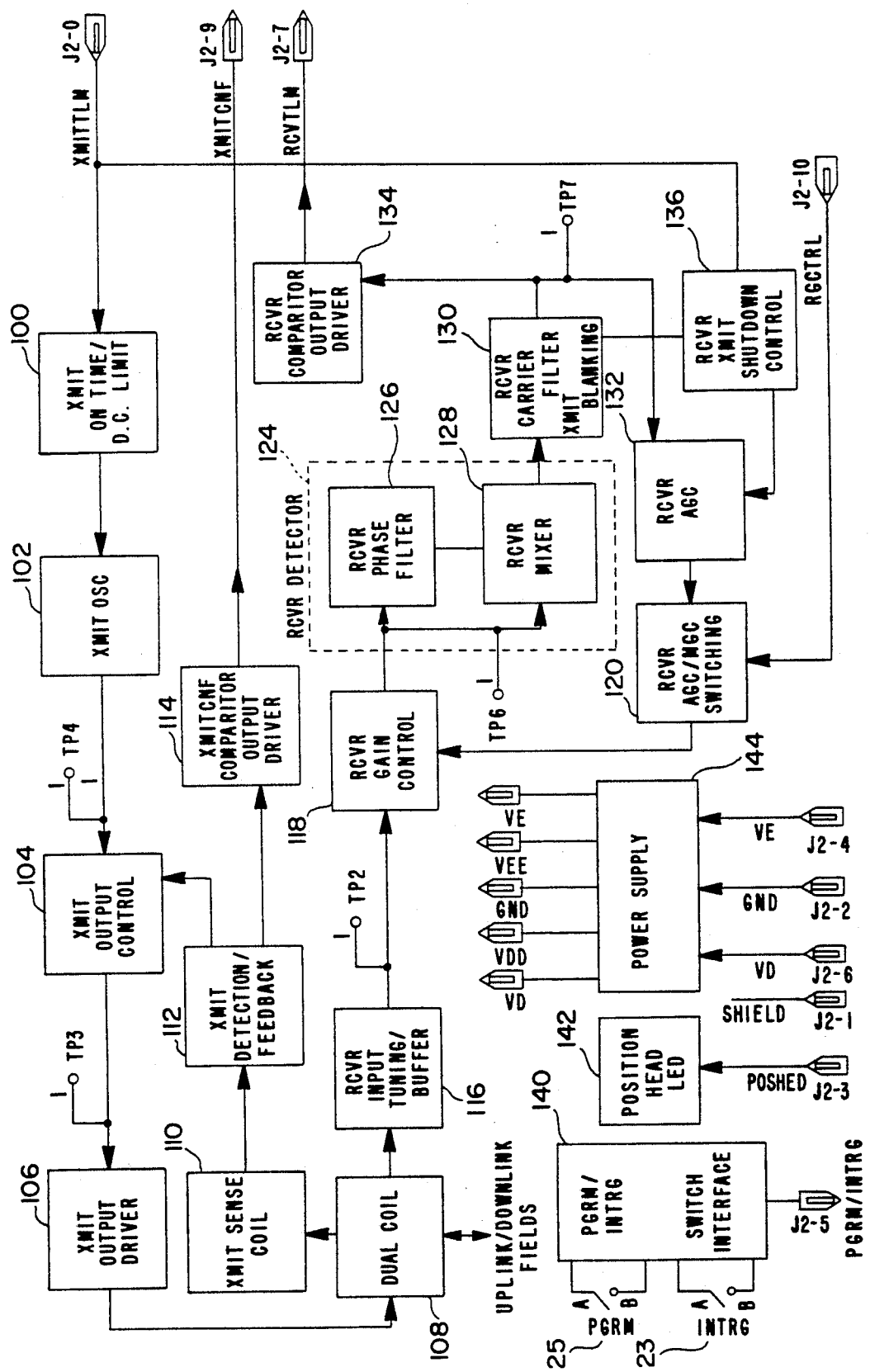
FIG. 4 is a functional block diagram of the RF telemetry transmission and receiving circuitry and other components mounted within the Medtronic® Model 9765 programming head of the programming system of the present invention.
Figure 5:
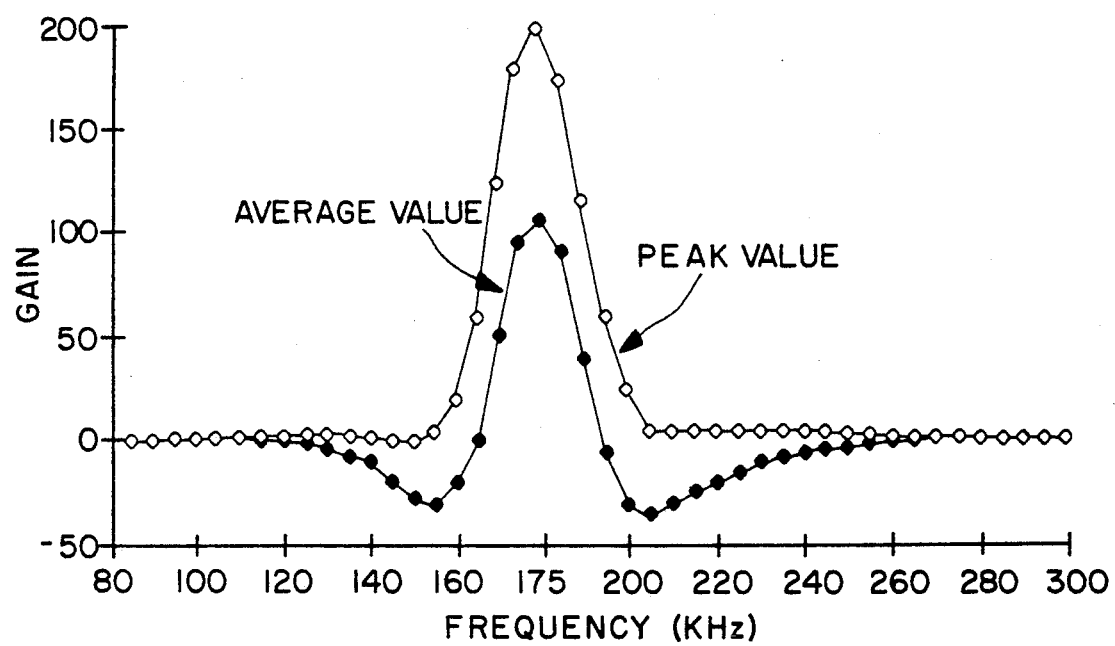
FIG. 5 depicts the frequency response of the improved detector circuit of the present invention.
Figure 6A:
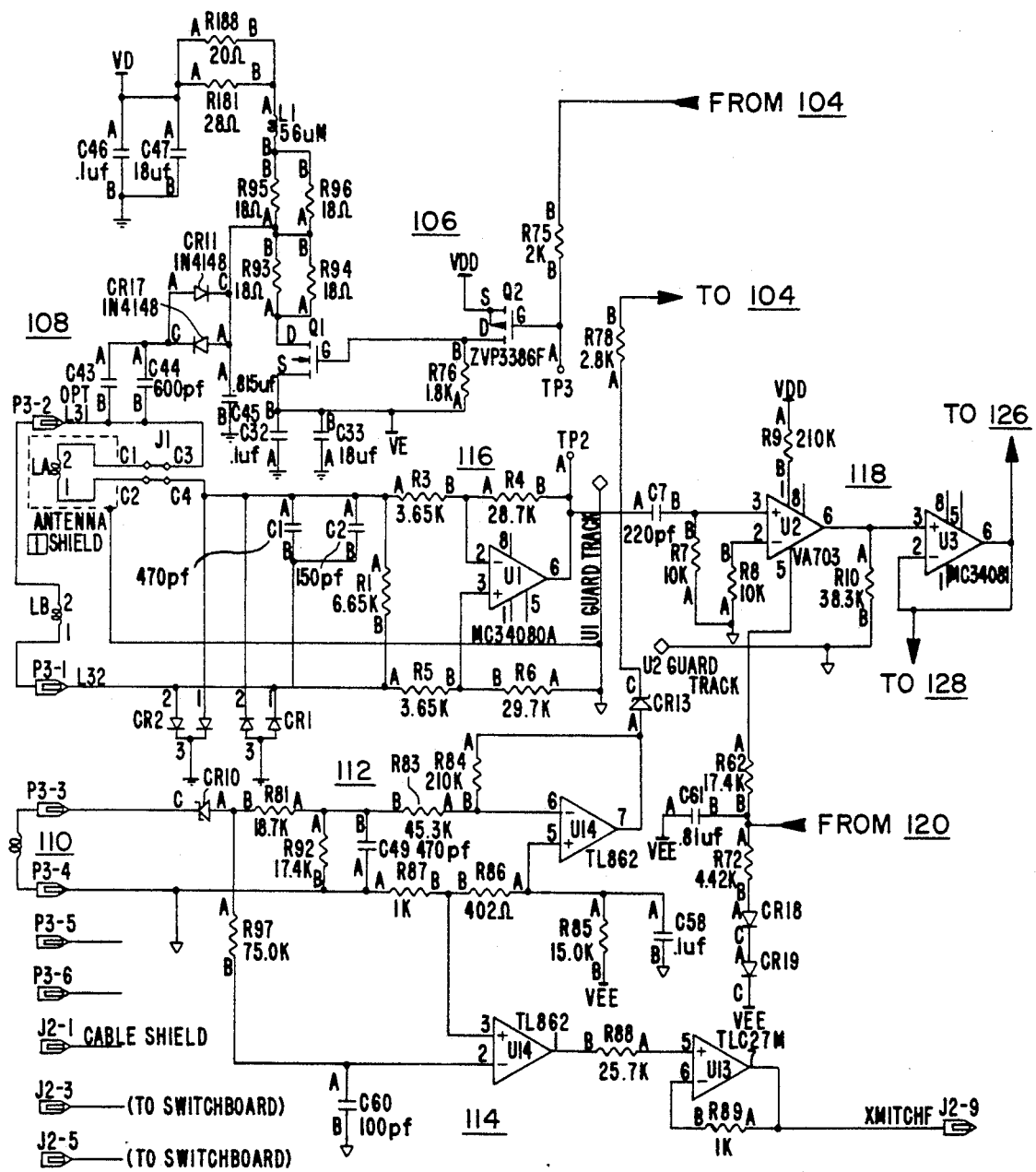
Figures 1, 6B:
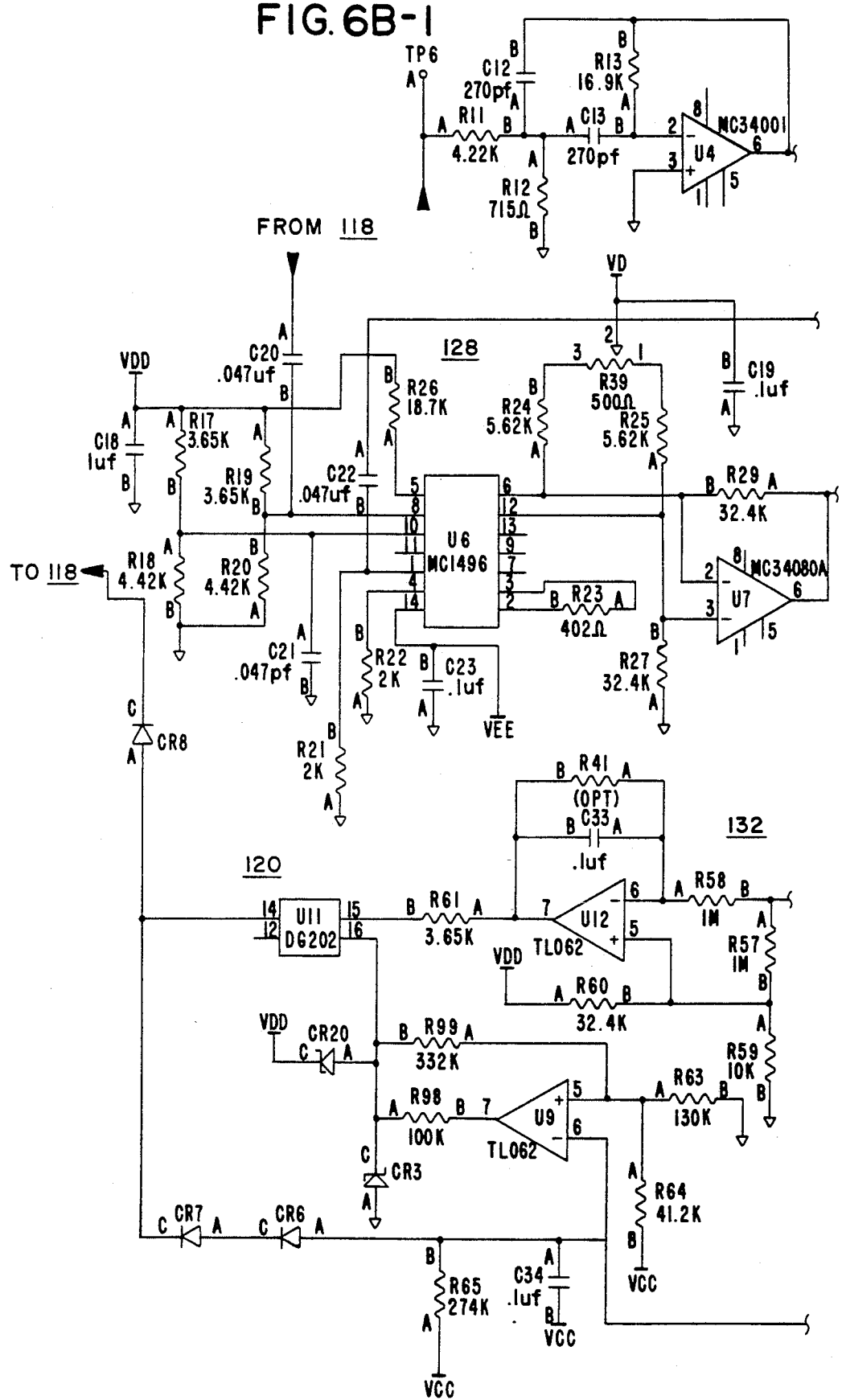
Figures 2, 6B:
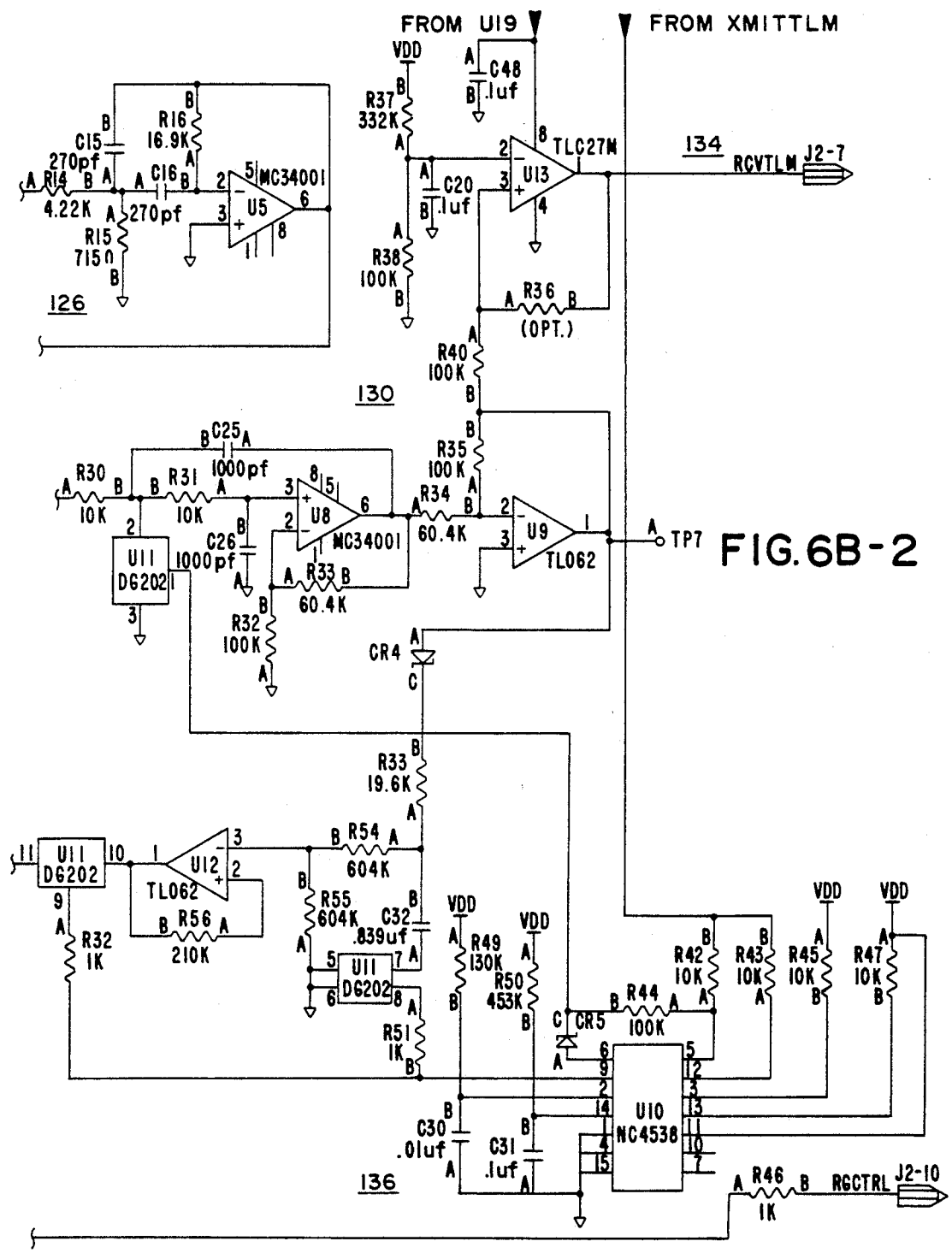

The enhanced transceiver circuit of the present invention and, in particular, the enhanced receiver detector of the present invention are shown and described in detail in conjunction with FIGS. 4 to 6. Turning to FIG. 4, it depicts in block diagram form the blocks of the transceiver circuit as well as the input and output signals exchanged between the programmer central processing unit and the positioning head 14 labelled at terminals J2-1 to J2-9. Certain test points used in manufacturing are indicated by the "TP" designation.

Figure 1:
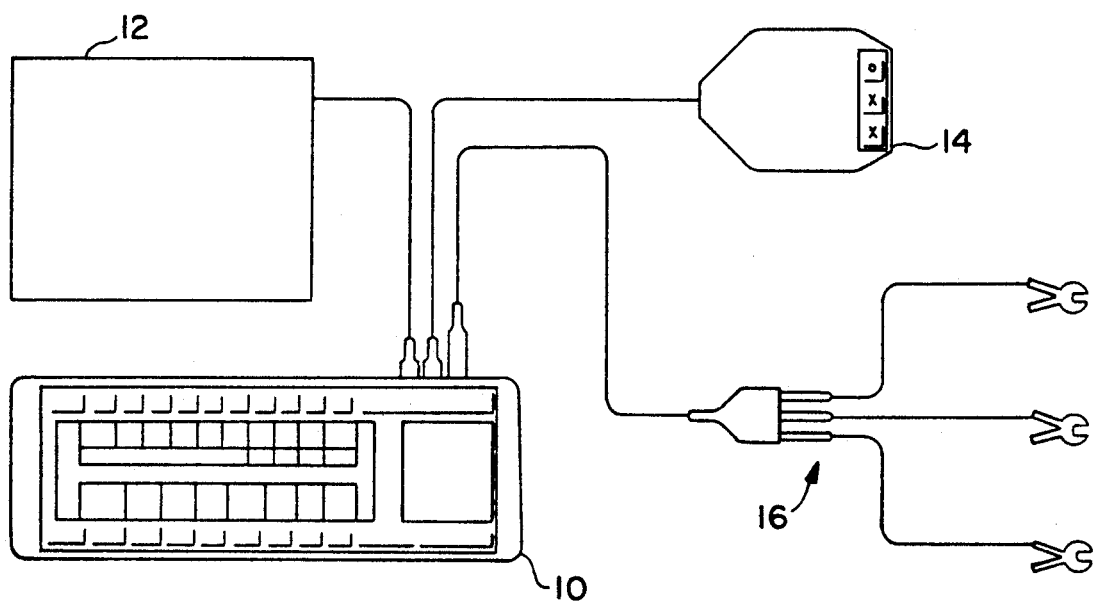
FIG. 1 depicts the programmer-system hardware of the prior art in which the improved transceiver circuit of the present invention may be implemented.
Figure 2:
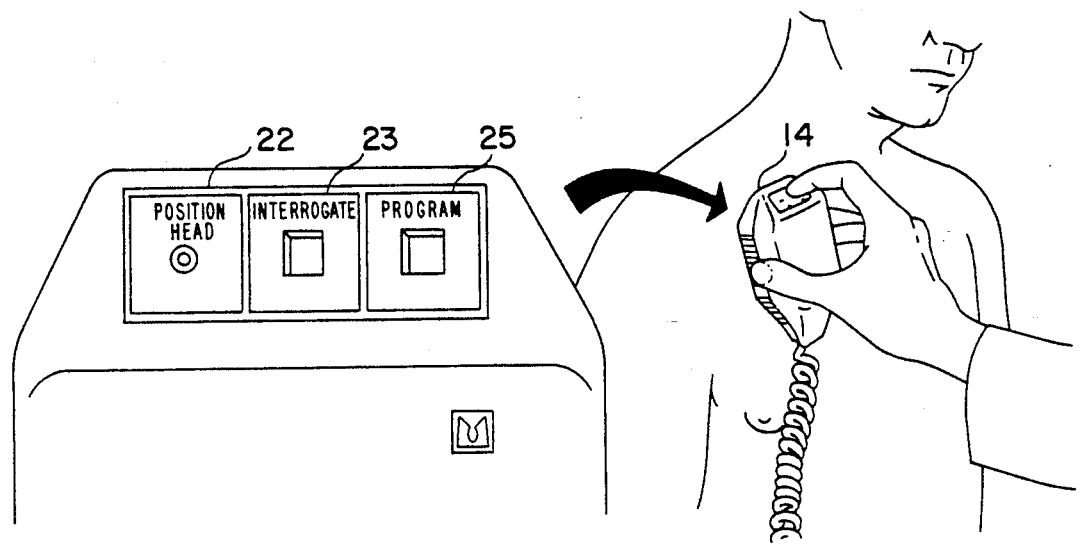
FIG. 2 depicts prior art positioning of the programming head over the implanted pulse generator and the indicator light LED for indicating proper position for both programming in and telemetry out from the implanted pulse generator.
Figure 3:
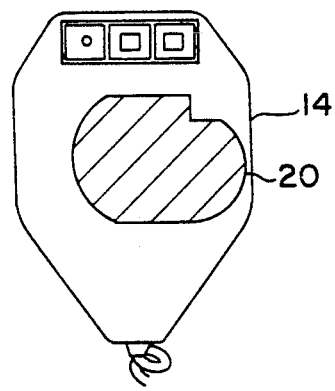
FIG. 3 depicts a typical prior art programming head position in relation to the implanted pulse generator.

The programming head 14 depicted in FIGS. 1, 2 and 3 also possesses a pair of push button switches 23 and 25 labeled INTERROGATE and PROGRAM respectively. In use, the physician depresses one or the other of the two buttons as shown in FIG. 2, and those depressed buttons control the overall function of the transceiver circuit of FIGS. 4 and 6A–6C. The INTERROGATE and PROGRAM buttons 23 and 25 are depicted in FIG. 4 coupled to the program/interrogate switch interface block 140 which provides the respective signal via terminal J2-5 to the central processing unit of the programmer 10.

The switch interface block 140 provides either a PROGRAM or INTERROGATE command signal depending on which of the two buttons is being depressed by the user at the time. The signal that is transmitted out of block 140 back to the programmer 10 allows telemetry in (or uplink telemetry) and telemetry out (or downlink telemetry) to take place under command of data entered by the user into the programmer 10.

The block diagram of FIG. 4 includes the transmission blocks labeled 100, 102, 104, 106, 108, 110, 112, 114 and 136. Essentially, when a transmit telemetry (XMITTLM) signal is received at terminal J2-8, it provides downlink telemetry from the dual antenna coil block 108, a transmit confirmation (XMITCNF) signal via terminal J2-9 back to the programmer 10, and blanks or shuts down the receiver portion of the circuitry the receiver output signal and freeze the receiver automatic gain control during downlink telemetry.

The receiver section includes the blocks 108, 116, 118, 120, 124, 126, 128, 130, 132 and 134 which continually process any detectable uplink telemetry present when not operating in the downlink telemetry mode. A receiver gain control signal (RGCTRL) applied via terminal J2-10 or the receiver automatic gain control signal developed by block 132 are employed to set the receiver gain in block 118 in a fashion to be described in greater detail later.

The remaining components of the block diagram of FIG. 4 include the position head LED block 142 which responds to a position head input signal (POSHED) at terminal J2-3 to light up as long as the programming head 14 is not properly positioned over the implanted pulse generator 20 as shown in FIG. 3.

The power supply block 144 provides isolated, regulated power supplies for different portions of the circuit in order to avoid interference between the transmitting and receiving portions of the circuitry through either the power supply positive voltage or ground lines as shown in FIGS. 6A–6C.

The circuit of the block diagram of FIG. 4 and the schematic diagram of FIGS. 6A–6C is surface mounted to a first 12 layer circuit board which also carries a first multi-layer antenna coil designated $L_A$ in FIG. 6A. Certain components of the electrical circuit are shielded from coil $L_A$ by metal foil or line or electrical shields within or on the first circuit board. Coil $L_A$ is formed in a number of layers and in a number of turns, with each layer and turn precisely positioned and spaced from the adjoining coil turn and coil layer to provide highly reproducible coil characteristics.

The second, matched antenna coil designated $L_B$ is similarly fabricated within a second 12-layer circuit board carrying shielding matched to that of the first circuit board but carrying no electrical components and spaced a predetermined distance therefrom to provide the dual antenna coil configuration of the aforementioned '532 patent wherein both antenna coils have virtually identical electrical characteristics. A torrodial permanent magnet is also situated within the programming head 14 between the two circuit boards and respective antenna coils to provide a fixed magnetic field in relation to the two antenna coils. The fixed magnet, as is well known in the art, is provided to close the reed switch within the implanted pulse generator.

Returning to FIG. 4, the aspect of the description of particular interest to the present invention is contained within the block 124 of the receiver section in conjunction with the remaining components of the receiver section. Very generally speaking, the dual antenna coil block 108 is configured in the same fashion as the coils 22, 24 and diodes 34, 36, 38 and 40 of the '532 patent and operates as described therein. The characteristics of the circuits of blocks 108 and 116 are such that the antenna coil tuned antenna circuit is resonantly tuned to 128 kHz, well outside the 175±25 kHz frequency of interest of the telemetered, RF signal, so that the tuned antenna circuit will "ring", in response to a transient signal, well outside the bandpass characteristics of the receiver detector block 124. In effect, the receiver detector 124 is blind to such signals as described hereinafter. The output signal of the block 116 is applied to the receiver gain control block 118 which, as stated hereinbefore, amplifies the signal as a function of the automatic or manual gain control (AGC or MGC) value applied thereto by block 120.

The dual coils $L_A$ and $L_B$ of block 108 are operating in a series opposing configuration, the output of which is sent to receiver input tuning buffer block 116. An output signal is then sent to a receiver gain control block 118 which is then processed by the receiver detector 124 which utilizes an active mixer 128 and a phase shifting network 126. The output of the detector is then processed by a carrier filter 130 providing the resulting demodulated uplink signal a TP7. This signal is then sent to the receiver comparator output buffer driver 134 which provides a high level output signal which is transmitted down the cable to the programmer 10.

The receiver gain operating level is controllable in two modes. These modes are referred to as automatic gain control (AGC) and manual gain control mode (MGC). The mode in use is controlled by the receiver gain control signal (RGCTRL). When operating in the AGC mode, the signal from PT7 is used by the receiver AGC block 132 to generate a controlling signal delivered to the receiver gain control block 118. When operating in the MGC mode, the receiver gain is controlled by a DC current level delivered by the programmer at the RGCTRL terminal (J2-10). The RGCTRL terminal also controls which mode the 9765 is operating in. When the current into this terminal is at zero microamps, the device will be operating in the AGC or automatic gain control mode.

Turning now to the inventive receiver detector block 124 of the present invention, it includes the receiver phase filter 126 and receiver mixer 128. The receiver phase filter 126 effects no phase shift for incoming signals of interest, and up to ±180° of phase shift to signals outside the frequency band of interest and applies it to on input of the receiver mixer 128. The receiver mixer 128 receives the original signal at its other input and as the two signals are mixed, a DC output signal is produced with an amplitude and polarity which is a function of frequency. Signals outside of the range of interest centered at 175 kHz produce a positive going response at the detector 124 output. Signals within the frequency range of interest between 150 to 208 kHz produce a negative going response. Signals of interest at 175±12.5 kHz are amplified with up to a 30 decibel gain. The resulting DC signal is applied to the input of the receiver carrier filter 130 which demodulates the signal, and the resulting envelope signal as shown in FIG. 5 is applied to the input of the receiver comparator output driver 134. The demodulated signal is compared against a reference signal at the receiver comparator output driver 134 to develop a limited rise time and fall time square wave RCVTLM signal which is applied via the received telemetry line and terminal J2-7 to the programmer.

The output signal of the receiver carrier filter block 130 is also applied to the input of the receiver AGC block 132 which develops the AGC signal value for controlling the gain of the receiver control amplifier 118. As stated hereinbefore, the AGC signal or the MGC RGCTRL signal is applied to the receiver gain control 118 depending on the state of the receiver AGC/MGC switching block 120.

Returning to FIG. 4, the receiver detector 124 effects a reject band outside the 148 208 kHz range. The receiver antennae therefore are tuned below 150 kHz with a Q still high enough to allow reasonable amplitude response at 175 kHz. Transient noise exciting the antennae produces a ringing response at the tuned frequency. The noise response of the antenna stimulates the detector to produce a desired inverted output. As the transient amplitude increases, the inverted response increases in amplitude, driving the detector 124 output level further away from the trigger level of the post detection comparator block 134. Any steady state noise signal in the reject band will also result in a steady state inverted detector 124 response which will not trigger the comparator output driver 134 in the absence of a sufficiently strong signal within the frequency range of interest.

Returning to the transmitter, the Model 9765 transmitter is shown in the upper portion of the block diagram illustrated in FIG. 4. The transmitted signal is a 175 kHz RF pulse which is keyed ON and OFF by the XMITTLM signal delivered from the programmer at terminal J2-8. The XMITTLM signal is passed through an ON-time and duty cycle limit circuit 100 before it is allowed to key the transmit oscillator 102 ON. The XMITTLM signal also is delivered to a transmit shutdown controller 136 located in the receiver portion. Block 136 serves to blank the receiver output of block 130 and freezes the AGC value in block 132 during transmit operation.

. Valid XMITTLM signals that are able to pass through the ON-time and duty cycle limit circuitry 100 will key the transmit oscillator 102 ON. The 175 kHz oscillation signal is passed through a transmit output control circuit 104 which operates the transmit output driver 106. The output driver 106 is a Class C driver which drives the dual antenna coils in a parallel aiding configuration to generate a strong H field output. In the second printed circuit board, the transmit sense coil 110 receives a portion of the signal which is fed back to a XMIT detection circuit 112 which develops feedback signal applied to transmit output control 104. The output control circuit 104 controls the efficiency of the transmit output driver 106 and compensates for variations due to power supply changes, components, and also load conditions that are presented to the dual antennae coil block 108 due to varying locations of the implanted pulse generator 20 as described in my copending U.S. Patent application Ser. No. 07/611,900, filed Nov. 9, 1990.

The ON time/D.C. limit block 100 protects the downstream components of the transmitter from being damaged in the event that an invalid steady state XMITTLM signal is received at terminal J2 8. An input signal remaining high for a predetermined period of time or exceeding a certain duty cycle between input signals is blocked from triggering the transmit oscillator 102.

When triggered by a proper XMITTLM input signal, transmit oscillator block 102 provides a 175 kHz signal to the transmit output control 104 which produces controlled pulse width signals (at fixed 5.71 microsecond pulse intervals) which are applied to the transmit output driver 106 which in turn synchronously excites the parallel resonant LC tuned antenna circuit, formed by antennae $L_A$ and $L_B$ and capacitor C44. The current developed in the dual coil circuit generates the 175 kHz sine wave, magnetic field, downlink telemetry. The intervals between bursts define the pulse interval or position modulated data transmitted to the implanted device.

As shown in the aforementioned Medtronic '884 patent, the transmission sensing coil 110 is situated within the programming head 14 (on the second printed circuit board) to pick up the magnetic field of the transmission output driver circuit 106 and dual coil 108 and apply it to a transmit detection/feedblock block 112. One output of the Block 112 is applied to a transmit confirmation comparator output driver 114 which in turn supplies a transmit confirmation signal (XMITCNF) out pin J2-9 to the programmer 10 to confirm the telemetry out of a XMITTLM command.

Turning now to FIGS. 6A-6C, the schematic diagram of the Model 9765 programming head transceiver circuit is depicted and described as follows:

Receiver Input Circuitry 116

The receiver input circuitry 116 involves the portion of the schematic of FIG. 6A from the $L_A$ and $L_B$ coils to TP2. The antenna coils La and $L_B$ are connected via E1-E3 and E2-E4 in a series opposing configuration for telemetry uplink reception. In the receive mode, diodes CR1, CR2, CR11, and CR17 remain off, thereby providing isolation of the receiver input from the transmitter circuitry. Using the net mutual inductance of $L_A$ and $L_B$, the input circuit is tuned with capacitors C1, C2 and resistor R1 in parallel with the input impedance of the U2 buffer circuit. The receiver input is tuned to approximately 128 kHz even though the signal of interest at the receiver is 175 kHz. The reason for this will be explained later in the detector circuit discussion. Differential amplifier U1 buffers the input and provides approximately 15 db gain. There are various guard tracks as indicated on the schematic (U1, U2 guard track) that connect to the antennae E-shield. These tracks are used to improve isolation between the sensitive input circuit and other circuit components. Amplifier U1 is heavily decoupled from the power supply to provide a good margin of power supply isolation.

Receiver Gain Control Circuitry 118

The receiver gain control circuitry 118 is located between test points TP2 and TP6 in FIG. 6A-6B. This circuit utilizes an OTA (operational transconductance amplifier) designated as U2. Operational amplifier U3 comprises a unity gain buffer to drive the detector input signal at TP6 (FIG. 6B) for the next stage. The gain of OTA U2 is controlled by the current into pin 5. This current is supplied from the AGC control circuit explained hereafter in reference to FIG. 6B.

Receiver Detector 124, 126, 128

The receiver detector 124, 126, 128 (FIGS. 4 and 6B), in conjunction with the receiver input design produces a very selective detector for signals within the desired pass band while providing a high level of rejection for both transient noise and out-of band steady state noise. The detector incorporates an active mixer 128 and a precision-tuned active phase shifting network 126. This combination provides level signal rectification, precise narrow bandpass filtering, as well as 30 db amplification. The only calibration required is an offset calibration controlled by resistor R39.

The detector takes the received signal at TP6 in an unbalanced fashion and mixes it with a phase shifted version of the same signal from TP6 to produce a detected negative going DC component at U7-6 which is a function of frequency. The DC response emulates a system having a narrow 25 kHz bandpass filter operating at 175 kHz, but does not share the same degree of undesirable transient response associated with such narrow filters. For signals in the reject band, the output at U7-6 is a signal of opposite polarity to the desired signal polarity.

The necessary phase shifting is accomplished with two active bandpass stages comprising amplifier stages U4 and U5. Both stages are identical, with each providing 6 db of gain at 175 kHz. The Q (2.67) of each stage of the phase shift network is designed to produce the correct amount of phase shifting necessary to yield the simulated 25 kHz bandpass filter characteristic after the mixing process. The phase shifting filters (U4, U5 and associated components) are constructed with one percent metal film resistors and NPO capacitors for the necessary temperature stability. The filter op amps U4, U5 (Motorola MC34081) were selected for their high gain band width product for the operating supply current required. The finite open loop gain of the op amps U4, U5 is low enough to require compensation to achieve the precision necessary to avoid calibration. This compensation is accomplished by using a center frequency design value shifted by the same percentage as the theoretical open loop phase error expected for this op amp. The output of the phase shifting network amplified by a total of 12 db (at 175 kHz) is then presented to the input of the U6 mixer in an unbalanced mode.

The mixing process at U6 provides approximately 30 db of gain and yields a signal having twice the frequency of the input signal. Additional gain of approximately 6 db is provided by the U7 output buffer. For the 175 kHz signal of interest, the output of the phase shifting network is an unphase shifted signal which when mixed with the input signal at TP6 produces a rectified signal at U7-6 with a DC component going in the negative direction. Signals above and below 175 kHz are shifted either positive or negative, producing a mixing result yielding a lower amplitude signal at U7-6. For signals below 148 kHz and above 208 kHz, the phase shifting is sufficient enough to produce a positive going signal at U7-6.

This detection process combined with the receiver input coil transient characteristics provides a transient noise immunity as follows. Transient noise pulses in either the H or E field mode exciting the input coils $L_A$ and $L_B$ results in a natural resonant frequency ringing of the input tuned frequency, i.e., 128 kHz. This signal is amplified in a wide band fashion and presented to TP6. The 128 kHz noise at TP6 is phase shifted sufficiently enough by the phase shifting filter so as to produce a positive going result at the detector output U7-6. For the case of steady state noise signals that are outside the 148-208 kHz band, the result is a steady state positive DC offset at U7-6. In both cases, the response at U7-6 serves to drive noise signal away from the comparator threshold level, thereby reducing the threat of a false positive response to noise.

Carrier Filter 130

The detector output at U7-6 is processed by the carrier filter 130 comprising op amp U8 and associated circuitry to produce the demodulated uplink pulse. The carrier filter 130 is a 16 kHz low pass filter with dampening coefficient of 0.6. The filter design was chosen to yield a high level of carrier ejection without introducing excessive group delay distortion. The MC34081 op amp (U8) is chosen to provide good filter behavior to 500 kHz.

The analog switch U11-1 is positioned in the filter input to provide receiver blanking during transmitting to prevent unwanted RCVTLM pulses at the output J2-7. The output of the carrier filter is buffered with some amplification by the op amp U9-1 and provides a positive going signal at TP7.

Output Comparator 134

The demodulated signal at TP7, with a typical peak amplitude of 5 volts, is coupled to the output comparator circuit 134 comprising differential amp U13-1 and its associated components. The threshold level of the comparator is set to 1.16 volts. This relatively low threshold level is chosen to optimize overall performance by taking advantage of the characteristically clean base line of the receiver design. Under transient noise conditions, the detector block provides good suppression of false positive artifacts but false negatives are a different matter. When a transient noise burst occurs coincident with an uplink burst, the phase relationship of the two signals will determine whether the output amplitude will be enhanced or degraded. A nominal output level at TP7 for an uplink pulse is 5.0 volts. The relatively low 1.16 volt comparator threshold provides added margin against false negatives and is set at the level where both the false negatives and false positives begin to occur simultaneously for very large transient input noise levels, thereby optimizing overall receiver performance.

The mechanical construction of the Model 9765 requires the output pulse of the U13-1 comparator to be routed through a conductor passing across the turns of the $L_A$ input coil. The edges of this output pulse may couple into the input circuit causing feedback noise. To minimize this, E shielding is provided over the $L_A$ coil; and to minimize H field coupling of the output signal into the coil, the slew rate of this comparator has been limited. Additional decoupling of this signal into the receiver is accomplished by using the U19 reference from the transmitter circuit to power the U13 comparator for better power supply isolation.

Receiver Gain Control 132, 120

The Model 9765 receiver gain can be controlled in two modes: AGC (Automatic Gain Control) mode, and MGC (Manual Gain Control Mode). The mode in operation is controlled from the programmer by the receiver gain control line (RGCTRL). To operate in AGC mode, the programmer sets the current on this line to 0 (i.e., :<5 microamps). To operate and control gain in the MGC mode, the receiver applies a current between 20 microamps to one milliampere.

The receiver's AGC control 132 is achieved with a second order feedback network that operates off peak detection of the demodulated signal at TP7 applied to capacitor C32 through diode CR4 and resistor R53 The advantage of attempting a second order AGC design is that assessing the stability of the device is simplified. Since the received signal is not a steady state signal but a transitory signal, the sampling process for the AGC must be done in such a fashion so as to compensate for the duty cycle. This is done by inversely controlling the charge and discharge of the C32 sampling capacitor so as to compensate for the duty cycle. When properly achieved, the DC voltage capacitor of capacitor C32 should equal approximately one-half the amplitude of the peak signal at TP7. Switch U11-8 is used to maintain the charge on capacitor C32 during transmit operations.

A proportional sample of the net resulting capacitor C32 voltage is sampled and buffered by U-12 (first stage). This signal at U12-1 is then sent to an integrator U12 (second stage), which produces a driving signal for the OTA U2 (FIG. 6A).

The two poles associated with the second order system are created by the sampling capacitor C32 network and also by the integrator U12.

During telemetry transmission, a signal from U10-9 is applied to switch U11-9 to render it open, and resistor R57 ties the integrator U12 (second stage) input to the reference created by resistor R59 to freeze the integration process during transmit operations.

The third U11-16 switch in block 120 responds to a signal at U11-16 to open or disconnect the AGC output circuit to allow manual gain control via the RGCTRL signal from the programmer. Op amp U9 is used as a switch to detect when the programmer is sending a current pulse of sufficient duration to switch the device into the MGC mode by opening switch U11 (block 120) at terminal U11-16. AGC operation is guaranteed for current levels on the RGCTRL input from 0 to 5 microamps. The switching process occurs between 5 and about 10 microamps, and sufficient receiver gain for normal operation is achieved over the range of 20 microamps to one milliampere. This current in the manual gain control mode is conducted through diodes CR6, CR7 to the same node (U11-14) as is driven by the AGC circuit. Diodes CR18 and CR19 simulate diode junctions as seen into pin 5 of U2, thereby providing easier design of the current divider created by resistors R62 and R72.

The receiver shutdown during transmit is controlled by the U10 dual monostable component. Both monostables in component U10 are triggered by the XMITTLM signal applied to U10 5 and U10-12. One monostable is set slightly under a one millisecond ON-time which controls U11-1. Resistor R44 and diode CR5 provide additional shutdown so that when the XMITTLM line goes high, U11-1 will close grounding the demodulator millisecond after the XMITTLM signal goes low, thereby providing a one millisecond blanking after the transmit operation. This is sufficient to prevent any false artifacts from being generated on the RCVTLM line due to the transmit signal, which is generated using the antenna coils $L_A$, $L_B$ coupled to the receiver input tuning/buffer 116.

The second monostable in U10, also triggered by the XMITTLM, is a 30 millisecond monostable, which controls U11-9 and U11-8. As mentioned before, these two monostables freeze the AGC circuit to its operating level prior to transmission The 30 millisecond timing is set so that between transmit blocks, for current downlink telemetry data formats, where no transmit pulses occur, the receiver AGC will be maintained at its level prior to the beginning of the transmission. Following the 30 millisecond timeout, the U11-9 and U11-8 switches are closed, and the AGC is allowed to integrate based on the signal at TP7.

Transmitter Circuit Details

The 9765 transmitter shown in FIGS. 6A and 6C is a closed loop 175 kHz burst transmitter which is keyed on and off by the transmit telemetry signal XMITTLM delivered from the programmer to terminal J2-8. The closed loop transmitter incorporates the sense coil 110 connected to terminals P3-3 and P3-4 which provides feedback to the transmitter controlling its efficiency to compensate for a variety of efficiency variables, including component variations, IPG antenna loading and power source variations. The sense coil 110 and driver 114 also provide the XMITCNF signal indicating transmit energy detected by the coil 110, which is usable by the program to verify that the transmitter did transmit, as described in the aforementioned '884 patent.

Transmitter Duty Cycle and ON Time Limit Circuit 100

The XMITTLM signal delivered from the programmer is a TTL level signal and is fed into the anode of CR15 of the transmit ON-time duty cycle limit circuit 100 (FIG. 6C). This circuit allows the signal to pass through, providing that the ON-time is under the maximum limit and that the duty cycle as averaged over an extended period of time does not exceed forty percent. The components serving this function are CR15, C35, R70, CR9, and R71. Valid signals passing through the circuit then go to the transmit oscillator circuit 102.

Transmit Oscillator 102

The transmit oscillator 102 is keyed on by valid transmit telemetry signals. The oscillator 102, comprises U15 and is powered with a separate supply via U19, a voltage reference source. Voltage reference source U19 provides a clean supply source for this critical circuit during transmit operations so as to provide a steady oscillator frequency of 175 kHz. This frequency is calibrated by resistor R26. The RC network for the oscillator 102 comprises components R26, R73, and C38. Capacitor C38 is a NPO capacitor chosen for good temperature stability. The output of the oscillator signal, seen at TP4, is coupled to the transmit output control circuit 104.

Transmit Output Control Circuit 104

The transmit output control circuit 104 provides a one-shot output transmit driver signal from monostable U16. The ON time period of the one shot is controlled by R74. C41 and a feedback signal from the transmit detection feedback circuit 112 applied to U16 2. The output pulse at pin 7 of the monostable U16 varies from under a microsecond up to three microseconds. This is controlled by the signal from the transmit feedback circuit 112 (FIG. 6A) which samples the H field generated by the transmitter and picked up on coil 110. The signal on coil 110 is half-wave rectified by components CR10, R81, R82, and C49. The sampled DC component representing the field strength being generated is fed back to the U16-2 node via op amp U14 at output 7 through diode CR13 and resistor R78. When the transmitter is initially keyed on by a XMITTLM signal, the output pulse width of monostable U16 is approximately 3 microseconds. This generates the highest driver output level to provide a fast rise time of the transmit envelope. When the output field strength approaches the desired level, current from the feedback network through R78 contributes to the charge of capacitor C41, thereby reducing the ON-time of monostable U16. Thereafter, the output pulse width decreases to a level usually below one microsecond. The interval between output pulses at pin 7 of monostable U16 is 5.71 microseconds.

Transmit Output Driver Circuit 106

The transmit output driver 106 (FIG. 6A) comprises components R75 through and including the antenna coils $L_A$ and $L_B$. The transmit output control circuit 104 delivers its pulse to the gate of FET transistor Q2, which inverts the pulse and drives the power FET transistor Q1. Transistor Q1 is operated as a class C output driver in conjunction with the tuned output L-C circuit comprising the inductance of L1 and the capacitance of capacitor C45, which provides high level excitation to drive the output antenna circuit comprised of $L_A$ and $L_B$ coils tuned with capacitor C44. The additional output resistors R93 through R96, R100 and R101 serve to provide protection for the more sensitive L1 surface mount inductor under heavy load conditions. They also reduce the Q of the output driver to prevent unwanted trailing edge envelope distortion due to energy coupled back in from the collapsing field of the $L_A$ and $L_B$ coils into the output driver circuit. Diodes CR11 and CR17 provide isolation of the output driver circuit from the coils $L_A$ and $L_B$ when used in the receive mode. During transmission, the diodes CR11 and CR17 are transparent to the output driver.

When transmitting, the printed circuit board coils $L_A$ and $L_B$ are driven in the parallel aiding configuration to generate the output H field. The tightly controlled construction of these coils results in one percent accuracy of the inductance. This allows tuning of the output antenna circuit with C44 without any calibration. Capacitor C44 is a one percent NPO high voltage capacitor.

During transmission, the voltage seen at terminal P3-2 can reach as high as 400 volts peak-to-peak. That node, which connects to coil $L_A$ pin 2 and coil $L_B$ pin 2, is the only part of the transmit circuit which is exposed to this high potential. Capacitor C45 and diodes CR1 and CR2 provide the conduction path for the oscillating current of the output tank circuit formed by the coils $L_A$ and $L_B$ and capacitor C44.

Transmit Confirmation Circuit 114

As stated earlier, the transmitted H field is sensed by the sense coil 110 in the second printed circuit board. This signal is rectified by diode CR10 and provides a signal at capacitor C60, which is applied to one input terminal of comparator U14. The comparator U14 output at U14-7 goes high when the transmit H field is above a level of approximately 6 db below the minimum required. The comparator output signal is then applied to an output driver 114 comprising op amp U13 and associated components. Op amp U13 has a limited slew rate characteristic desirable for transmitting the XMITCNF signal down the long cable to the programmer through terminal J2-9.

Power Supply Circuit (FIG. 6C)

The dual power supply lines from the programmer delivered to the programming head transceiver are received at terminal J2-6 and J2-4 (FIG. 4). A small amount of filtering is provided by the resistor R90, R91 and capacitors C51 through C54. This provides some filtering for the high $V_D$ and $V_E$ supply levels. Two regulators U18 and U17 provide positive and negative 5 volts ($V_{DD}$ and $V_{EE}$) for the remaining lower voltage circuitry.

Extensive power supply decoupling is provided for amplifier stages U1 and U2, associated with the receiver input circuitry. Less vigorous supply decoupling is provided for other circuit components as required.

Program/Interrogate Circuitry (FIG. 6A)

The program/interrogate switches 25, 23 (FIGS. 2 and 4) allows the user to remotely program or interrogate from the programming head 14 rather than from the programmer 10. These switches 25, 23, connect to a resistance network that utilizes the VD and VE supply levels from the programmer to generate the DC level on the program interrogate output (PGRM/INTRG) at terminal J2-5. The DC level provided to the programmer on the PGRM/INTRG line is a function of the switches depressed. Three unique voltages are given for each condition that is either one or the other, or both switches depressed.

CONCLUSIONS

The gain (30 dB) and the phase shifting characteristics of the detector stage 124 provide enhanced signal to noise detection while allowing processing of the predetected signal at very low levels. This is a necessary advantage over previous amount in view of the fact that all of the receiver processing is performed within and around the sensitive receiver input coils. Maintaining a low processing level while the signal is in its 175 kHz form reduces the devastating effects of capacitive and inductive feedback to the sensitive input coils that occupy a large physical area. This feature is especially critical in applications such as this where (due to the nature of the electromagnetic input and output fields)

shielding of such interference is usually not a viable option.

Although the preferred embodiments of the present invention have been described in the context of a Medtronic programming system, it will be appreciated that the following claims are not so limited or confined but are instead applicable to programming or telemetry systems of any manufacturer for any implantable medical device or implant. Those of skill in the art will be readily able to apply the teaching found herein to yet other embodiments within the scope of the following claims.

What is claimed is:

1. In a transceiver for transmitting and receiving radio frequency signals from an implantable medical device, said transceiver including a telemetry receiver comprising an inductive-capacitive tuned antenna circuit, signal detection means and signal discrimination means, and wherein said signals are representative of either analog or digital values and wherein said signals are induced in said inductive-capacitive tuned antenna circuit, the improvement in detecting and discriminating received data signals from noise signals comprising:

means for amplifying RF signals induced within said inductive-capacitive tuned antenna circuit and providing an amplified RF signal;

means responsive to said amplified RF signal for shifting its phase and for providing a phase shifted, amplified RF signal;

means for mixing said phase shifted, amplified RF signal with said amplified RF signal for providing a monophasic component of said mixed RF amplified signal, the amplitude of which is a function of frequency;

means for establishing a threshold amplitude value;

means for demodulating said monophasic component of said mixed RF amplified signal for providing a detected DC component of said RF amplified signal; and means for comparing the amplitude of said DC component with said threshold amplitude for providing a detected and demodulated output signal discriminated from noise signals, wherein said output signal represents implanted medical device performance characteristics or programming parameters.

2. The transceiver system of claim 1 wherein said phase shifting means comprises first and second matched active filter elements for phase shifting and amplifying said RF signal.

3. The transceiver of claims 1 or 2 wherein said inductance-capacitance tuned antenna circuit resonates outside a bandpass frequency range containing said received data signals.

4. The transceiver of claim 3 wherein said monophasic component of said mixed amplified RF signal has a first polarity for said amplified RF signals within a bandpass frequency range containing said received data signals and a second polarity for said amplified RF signals outside said bandpass frequency range.

5. A method for detecting and discriminating received radio frequency data signals from noise signals in a transceiver for transmitting and receiving radio frequency signals from an implantable medical device, comprising the steps of:

a. providing modulated data signals at a predetermined frequency;

b. adjusting a capacitor value within an inductive-capacitive tuned antenna circuit such that said antenna circuit resonates at a frequency below the predetermined frequency;

c. sensing said data and noise signals with said antenna circuit; and d. processing said sensed data and noise signals to discriminate said sensed data signals from said sensed noise signals.

6. The method of claim 5 wherein processing said sensed data and noise signals further comprises the steps of:

a. amplifying said sensed data and noise signals for providing a first amplified signal;

b. phase shifting amplified sensed signals occurring at frequencies below said predetermined frequency for providing a second amplified signal;

c. mixing said first amplified signal with said second amplified signal for providing a monophasic output signal, wherein said output signal has an amplitude and polarity which is a function of frequency;

d. demodulating said monophasic output signal;

e. inverting said demodulated signal;

f. comparing said amplitude of said inverted output signal with a predetermined threshold amplitude; and g. generating a square wave signal when said amplitude of said demodulated output signal exceeds said predetermined threshold amplitude, wherein said square wave signal is representative of said received radio frequency data signal.

7. The method of claim 5 wherein said predetermined frequency is about 175 KHz.

8. The method of claim 5 wherein said resonant frequency of said tuned antenna is about 128 KHz.

* * * * *